United States Patent [19]

Inaba et al.

[11] Patent Number: 5,324,868

[45] Date of Patent: Jun. 28, 1994

[54] METHOD FOR PREPARING 4,4'-BIPHENOL

[75] Inventors: Masashi Inaba; Norioki Mine; Mamoru Mizutani, all of Yokkaichi, Japan

[73] Assignee: Mitsubishi Petrochemical Company, Ltd., Tokyo, Japan

[21] Appl. No.: 66,180

[22] Filed: May 24, 1993

[30] Foreign Application Priority Data

May 29, 1992 [JP] Japan .................................. 4-139066

[51] Int. Cl.$^5$ ...................... C07C 37/50; C07C 39/12
[52] U.S. Cl. ...................................... 568/805; 568/730
[58] Field of Search ................ 568/730, 805, 730, 805

[56] References Cited

U.S. PATENT DOCUMENTS

| | | | |
|---|---|---|---|
| 4,891,453 | 1/1990 | Tanaka et al. | 568/730 |
| 4,950,808 | 8/1990 | Kowalczik et al. | 568/730 |
| 5,099,076 | 3/1992 | Takahashi et al. | 568/730 |

Primary Examiner—Werren B. Lone
Attorney, Agent, or Firm—Oblon, Spivak, McClelland, Maier & Neustadt

[57] ABSTRACT 4,4'-Biphenol is prepared through debutylation of 3,3',5,5'-tetra-tert-butyl-4,4'-biphenol in an organic solvent in the presence of an acid catalyst wherein the debutylation is carried out continuously using at least two reactors aligned in series, with a high yield and high purity on an industrial level.

18 Claims, 1 Drawing Sheet

METHOD FOR PREPARING 4,4'-BIPHENOL

BACKGROUND OF THE INVENTION

1. Field of the Invention

The present invention relates to a method for preparing 4,4'-biphenol. More particularly, the present invention relates to an economical method for preparing 4,4'-biphenol with high purity.

4,4'-Biphenol of the desired product to be prepared by the method of the present invention has recently been attracting a great deal of attention as a starting material for heat-resistant engineering plastics and the like. With the method of the present invention 4,4'-biphenol with enough purity for use as a raw material for these plastics can be prepared economically.

2. Description of the Background Art 4,4'-biphenol (referred to as BPL hereinafter) has been prepared by the following methods: alkali fusion of diphenyl disulfonic acid; hydrolysis of dibromodiphenyl; oxidative dimerization of 2,6-ditert-butyl phenol (referred to as 2,6-DTBP hereinafter) to 3,3',5,5'-tetra-tert-butyl biphenol (referred to as TBBPL hereinafter) and subsequent debutylation thereof; and the like. In the former two methods severe reaction conditions are required and separation of large amounts of, inorganic salts used in these reactions from the products is difficult, and therefore the oxidative dimerization of 2,6-DTBP is most preferably used to prepare BPL on an industrial level.

However, the process to produce BPL through the 2,6-DTBP route has not yet been fully economical or effective, particularly because the debutylation reaction has been proceeded in a batch process. The major problem of the debutylation reaction is the large endothermic reaction which requires large amounts of heat input to proceed with the reaction.

Consequently, the batch reactor requires a large of heat supply capacity to get high yields and quality of BPL. On the other hand, continuous processes using one reactor, which have never been known to give high yields with good quality, require very severe conditions, such as high temperatures, long detention time, and high concentrations of catalysts, which cause low selectivity and low quality of BPL.

SUMMARY OF THE INVENTION

As a result of intensive research to overcome the above-mentioned problems, the present inventors have found that the debutylation rates of the four butyl groups in TBBPL are not equal, and that the rate slows as the number of butyl groups decreases. Therefore, the heat input required for the first debutylation reaction is fairly different than that for the last one. Accordingly, continuous debutylation of TBBPL using reactors separated to two or more steps in series can produce BPL with a high yield and high purity continuously on an industrial level.

The present invention is a method for preparing 4,4'-biphenol through debutylation of 3,3',5,5'-tetra-tert-butyl-4,4'-biphenol in an organic solvent in the presence of an acid catalyst wherein the debutylation is carried out continuously using at least two reactors aligned in series.

The addition of portions of the acid catalyst to each step increases the yield and purity.

Accordingly, an object of the present invention is to provide a method for preparing BPL, in which debutylation of TBBPL in two or more separate reactors is carried out by adding portions of an acid catalyst to each reactor, with a high yield and high purity on an industrial level.

DETAILED DESCRIPTION OF THE INVENTION

Materials

Figure 1:
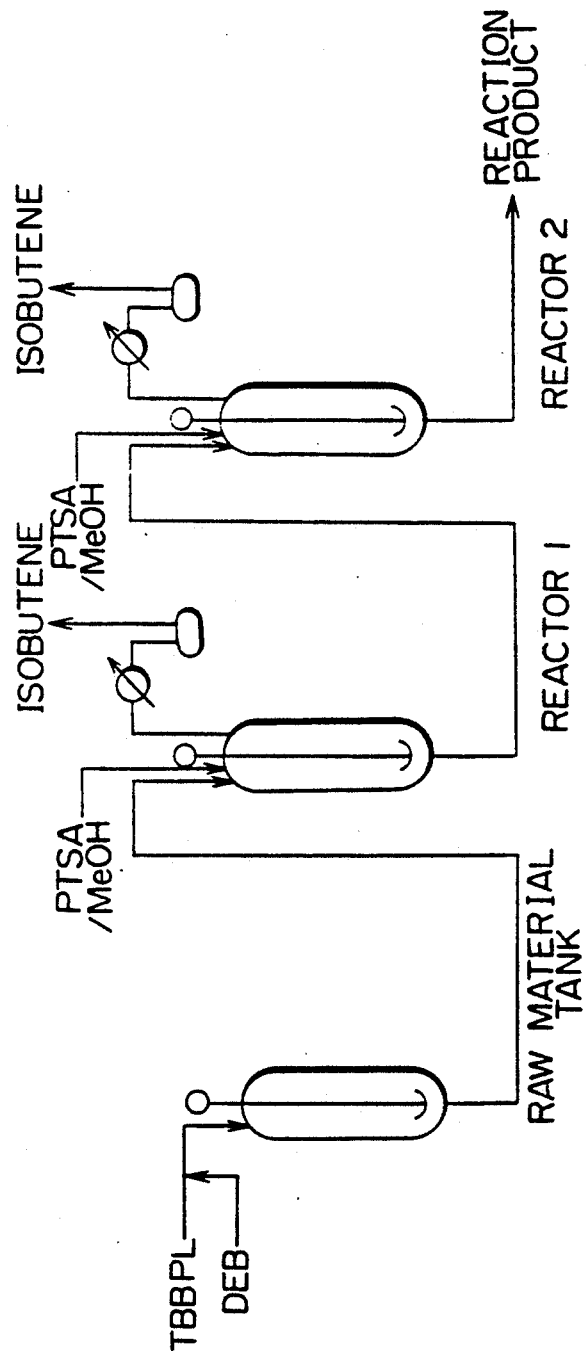
FIG. 1 is a flow diagram showing one of the methods according to the present invention.

The TBBPL used in the present invention can be obtained by the oxidafire dimerization of 2,6-DTBP, but the preparation method thereof is not limited.

TBBPL is usually continuously fed to the reactor in solution. Since the debutylation is an endothermic reaction, the raw materials are preferably preheated up to near the reaction temperature before being fed to the reactor.

Catalysts

The method of the present invention uses an acid catalyst as a debutylation catalyst. Examples of the acid catalyst include sulfonic acids such as p-toluenesulfonic acid and sulfuric acid; and Lewis acids such as aluminum chloride, iron chloride and aluminum phenoxide.

The amount of the acid catalyst used is 0.1–20% by weight relative to the amount of the raw material TBBPL, and preferably 0.5–5% by weight.

In the method of the present invention, an acid catalyst is added continuously, and preferably added in portions to each reactor. The ratio of the portions is not limited, and thus an equal amount of acid catalyst may be added to each reactor. When the acid catalyst is added by such method, the catalyst concentration becomes higher in the down stream side than in the upper stream side in the series of reactor, to improve the yield and quality of the products.

Further, adding the catalyst as a solution of lower aliphatic alcohol such as methanol and the like or water rather than adding the catalyst itself is preferable for producing BPL with a high yield and high purity. It is deduced that such effects are attained by better catalyst dispersion and isobutene elimination. It is also possible to mix the catalyst with TBBPL solution before it is fed to the reactor.

Solvents

The method of the present invention uses organic solvents in the debutylation reaction. The kind of such solvent is not intended to be limited; however solvents which meet the following requirements are preferably used:

1. A boiling point of 100° C. or higher because the reaction should be carried out at a temperature of at least 100° or higher;
2. To dissolve the raw material TBBPL relatively well; and the like.

Examples of the solvents include substituted aromatic compounds such as chlorobenzene, toluene, xylene, ethylbenzene, isopropylbenzene, tert-butylbenzene, diethylbenzene, isopropylbenzene, di-isopropylbenzene, naphthalene, and methylnaphthalene; paraffins such as decalin, undecalin and tridecalin; and paraffin mixtures such as gas oil and the like.

The amount of the solvent used is 0.5-10 parts by weight relative to the amount of TBBPL, and preferably 1-5 parts by weight.

Reaction Conditions

The reaction can be carried out in the temperature range of 100°-220° C. in each reactor, and preferably in the range of 130°-200° C. Lower temperatures than that increase the reaction time, while higher temperatures causes the product to deteriorate and color. Further, the reaction is carried out preferably with the reaction temperature increasing from reactor to reactor so that high quality BPL can be obtained with high yield.

The reaction can be carried out in a pressure range of 0.1-3 arm in each reactor, and preferably in the range of 0.7-1.5 arm.

FIG. 1 is an example of a flow diagram in accordance with the present invention. TBBPL and diethylbenzene (herein after referred to as DEB) are fed to the raw material tank attached a stirring and heating apparatus to dissolve TBBPL in DEB to prepare the feed solution.

The debutylation reaction is continuously carried out in reactor 1 and reactor 2 which are supplied enough heat for the endothermic debutylation reaction in each reactor. Vaporized DEB and the like are trapped by an overhead condensor and vessel, and isobutene which is generated by the butylation is not substantially condensed and vented away through a vent connected to the vessel.

Reaction product is continuously drawn out from the bottom of reactor 2.

In the method of the present invention, the debutylation of TBBPL is carried out continuously using two or more reactors aligned in tandem, and preferably from an economic and reaction-controlling point of view, carried out using two to five reactors.

In terms of detention time of the reaction mixture in the reactors, a total detention time of 1-15 hours in any reactor is suitable and about 2-10 hours is preferable. The detention time in each reactor is set depending on selection of the conversion rate in each step; thus it is preferable that the detention time in downstream reactors be set relatively shorter to achieve good yield and quality.

EXAMPLES

The method of the present invention will be illustrated with reference to the following examples, but the invention is not intended to be limited only to these following examples.

EXAMPLE 1

Stirring type of reactors 1 and 2 (each having a volume of 5 L) with jackets were connected as shown in FIG. 1. A solution of TBBPL in diethylbenzene (DEB) and a solution of p-tuluenesulfonic acid (PTSA) in methanol (MeOH) were fed to each reactor continuously under the conditions shown in Table 1 to cause debutylation. The effluent stream of reactor 2 was cooled down continuously to room temperature, and the precipitated BPL was separated from the solution using a centrifugal separator. The resultant precipitate was rinsed with pure water, and dried using a vacuum dryer to obtain white BPL with a yield of 86%.

This product was analyzed using a gas chromatograph and found to be 99.99% pure. Further, a 5% solution of the obtained crystal in methanol was evaluated for hue by measuring absorbance with a Shimazu UV-2100 spectrophotometer at 400 nm. Measured in a quartz cell 10 nm thick, the product had an absorbance of 0.042.

EXAMPLE 2

Using three reactors, i.e. the two reactors in Example 1 plus one reactor as one step (not shown in the Figure), the debutylation was continuously carried out under the conditions shown in Table 1 as in Example 1.

Reactor output solution was continuously cooled down to room temperature, and the precipitated BPL was separated from the solution using a centrifugal separator. The resultant precipitate was rinsed with pure water, and dried using a vacuum dryer to obtain white BPL with a yield of 90%.

This product was analyzed using a gas chromatograph and found to be 99.99% pure. Further, a 5% solution of the obtained crystal in methanol showed an absorbance of 0.035.

COMPARATIVE EXAMPLE 1

Using only a single reactor instead of the two reactors used in Example 1, the debutylation was carried out under the conditions are shown in Table 1 to obtain pink BPL with a yield of 73%.

This product was analyzed using a gas chromatograph and found to be 99.87% pure. Further, a 5% solution of the obtained crystal in methanol showed an absorbance of 0.228.

EXAMPLE 3

Using three reactors in series as in Example 2, the debutylation was carried out. However, all catalyst was fed to the first reactor alone. Reaction conditions are shown in Table 1, and pale violet BPL was obtained with a yield of 81%.

This product was analyzed using a gas chromatograph and found to be 99.87% pure. Further, a 5% solution of the obtained crystal in methanol showed an absorbance of 0. 186.

EXAMPLES 4 AND 5

Using three reactors in series as in Example 2, the debutylation was carried out under the conditions shown in Table 2. The results are also summarized in Table 2.

TABLE 1

| Conditions | Reaction Conditions of Debutylation | | | |
| --- | --- | --- | --- | --- |
| | Example 1 | Example 2 | Comparative Example 1 | Example 3 |
| feed rate* of TBBPL:DEB (g/hr) | 900 | 900 | 900 | 900 |
| feed rate** of PTSA:MeOH (g/hr) | | | | |
| 1st step | 9.0 | 6.0 | 18.0 | 18.0 |
| 2nd step | 9.0 | 6.0 | | 0 |
| 3rd step | | 6.0 | | 0 |
| reaction temperature (°C.) | | | | |
| 1st step | 180 | 180 | 180 | 180 |
| 2nd step | 180 | 180 | | 180 |
| 3rd step | | 180 | | 180 |
| detention time (hr) | | | | |
| 1st step | 2.25 | 1.5 | 4.5 | 1.5 |
| 2nd step | 2.25 | 1.5 | | 1.5 |

TABLE 1-continued

| Conditions | Reaction Conditions of Debutylation | | | |
|---|---|---|---|---|
| | Example 1 | Example 2 | Comparative Example 1 | Example 3 |
| 3rd step | | 1.5 | | 1.5 |

*TBBPL:DEB (weight ratio) = 1:1.25
**PTSA:MeOH (weight ratio) = 2:1

TABLE 2

| Conditions | Reaction Conditions and Results of Debutylation | |
|---|---|---|
| | Example 4 | Example 5 |
| feed rate* of TBBPL:DEB (g/hr) | 900 | 900 |
| feed rate** of PTSA:MeOH (g/hr) | | |
| 1st step | 6.0 | 4.5 |
| 2nd step | 6.0 | 6.0 |
| 3rd step | 6.0 | 7.5 |
| reaction temperature (°C.) | | |
| 1st step | 170 | 170 |
| 2nd step | 180 | 180 |
| 3rd step | 190 | 190 |
| detention time (hr) | | |
| 1st step | 1.5 | 1.5 |
| 2nd step | 1.5 | 1.5 |
| 3rd step | 1.5 | 1.5 |
| yield of BPL (%) | 92 | 91 |
| purity of BPL (%) | 99.99 | 99.99 |
| hue of BPL | 0.029 | 0.024 |

*TBBPL:DEB (weight ratio) = 1:1.25
**PTSA:MeOH (weight ratio) = 2:1

What is claimed is:

1. A method for preparing a 4,4'-biphenol comprising debutylation of 3,3',5,5'-tetra-tert-butyl-4,4'-biphenol in an organic solvent selected from the group consisting of chlorobenzene, toluene, xylene, ethylbenzene, isopropylbenzene, tert-butylbenzene, diethylbenzene, di-isopropylbenzene, naphthalene, methylnaphthalene, decalin, undecalin and tridecalin in the presence of a sulfonic acid catalyst or a Lewis acid catalyst, said debutylation being carried out continuously in from 2 to 5 reactors aligned in series.

2. The method as claimed in claim 1, wherein said sulfonic acid catalyst is selected from the group consisting of p-toluenesulfonic acid and sulfuric acid, and said Lewis acid is selected from the group consisting of aluminum chloride, iron chloride and aluminum phenoxide.

3. The method as claimed in any one of claims 1 or 2 wherein the amount of the acid catalyst used is 0.1–20% by weight relative to the amount of 3,3',5,5'-tetra-tert-butyl-4,4'-biphenol.

4. The method as claimed in any one of claims 1 or 2 wherein portions of said acid catalyst are added to each reactor.

5. The method as claimed in claim 4 wherein the acid catalyst concentration is increased from reactor to reactor along the series of reactors.

6. The method as claimed in any one of claims 1 or 2 wherein said reaction is carried out at a temperature range of 100°–220° C.

7. The method as claimed in claim 6 wherein the reaction temperature is elevated from reactor to reactor along the series of reactors.

8. The method as claimed in claims 1 or 2 wherein the total detention time of the reaction mixture in all reactors is 1 to 15 hours.

9. The method as claimed in claim 8 wherein said detention time of each reactor is reduced from reactor to reactor along the series of reactors.

10. The method as claimed in claim 3, wherein portions of said acid catalyst are added to each reactor.

11. The method as claimed in claim 3, wherein said reaction is carried out at a temperature range of 100°–220° C.

12. The method as claimed in claim 4, wherein said reaction is carried out at a temperature range of 100°–220° C.

13. The method as claimed in claim 5, wherein said reaction is carried out at a temperature range of 100°–220° C.

14. The method as claimed in claim 3, wherein the total detention time of the reaction mixture in all reactors is 1 to 15 hours.

15. The method as claimed in claim 4, wherein the total detention time of the reaction mixture in all reactors is 1 to 15 hours.

16. The method as claimed in claim 5, wherein the total detention time of the reaction mixture in all reactors is 1 to 15 hours.

17. The method as claimed in claim 6, wherein the total detention time of the reaction mixture in all reactors is 1 to 15 hours.

18. The method as claimed in claim 7, wherein the total detention time of the reaction mixture in all reactors is 1 to 15 hours.

* * * * *